United States Patent [19]

Johnston

[11] 4,362,745

[45] Dec. 7, 1982

[54] MEDICAL PROCESS AND PREPARATION

[76] Inventor: Frederick B. Johnston, 10901 Carrollwood Dr., Tampa, Fla. 33618

[21] Appl. No.: 324,106

[22] Filed: Nov. 23, 1981

Related U.S. Application Data

[63] Continuation-in-part of Ser. No. 208,286, Nov. 19, 1980, abandoned.

[51] Int. Cl.$^3$ .......................................... A61K 31/195
[52] U.S. Cl. .................................................... 424/319
[58] Field of Search ........................................ 424/319

*Primary Examiner*—Stanley J. Friedman
*Attorney, Agent, or Firm*—Arthur W. Fisher, III

[57] ABSTRACT

A medication and method of treatment for reducing tissue trauma in an animal, comprising the use of a N,N-dimethyl aspartic acid and/or N,N-dimethyl glutamic acid, physiologically acceptable salt or salts of either of the foregoing, and/or a mixture or mixtures of the foregoing, in which a suitable maskant such as benzyl alcohol may be included, the preferable method of treatment being a topical application to the skin to achieve penetration into the areas of tissue trauma.

12 Claims, No Drawings

MEDICAL PROCESS AND PREPARATION

CO-PENDING APPLICATIONS

The present application is a continuation-in-part to Ser. No. 208,286, filed Nov. 19, 1980, now abandoned.

BACKGROUND OF THE INVENTION

1. Field of the Invention

A medication and method of treatment for reducing tissue trauma in an animal, comprising the use of specific derivatives of amino acids.

2. Description of the Prior Art

Numerous efforts have been made to reduce or eliminate inflammation, edema generally associated with rheumatoid arthritis and other similar human dysfunctions. Perhaps the most widely known remedies are analgesics and more particularly salicylate compounds which act to reduce the inflammation and/or edema in the subject. In an effort to enhance the therapeutic properties of such analgesics or salicylates, efforts have been made to provide additional atoms, molecules, or such groups to the basic salicylate molecule.

Unfortunately, this technique or approach is directly in conflict with the three principal characteristics observed by this inventor as necessary to the enhancement of therapeutic compound sought. Specifically, the inventor, recognizing the need for a compound that would be able to be both lipid and water miscible and, therefore, able to penetrate the cell membrane as suggested by the Meyer-Overton Theory, and further, recognizing the advantage of chelation in the treatment of inflammation, with the concomitant reduction of edema and relief of pain, discovered that a family of low molecular weight amino acid derivatives offered the characteristics desired. This discovery constitutes the basic invention, i.e., the combination of oil-water solubility and miscibility, the penetrability of the cell membrane, and the sequestration chelation characteristic.

In seeking the therapeutic enhancement required, the inventor observed that a family of alkyl and/or dialkyl compounds exhibited unusually beneficial therapeutic effects, both pharmaceutically and physiologically. It was only through a unique combination of inter disciplinary knowledge and experience that this solution was discovered. Specifically, the discipline of biochemistry, combining organic and inorganic chemistry, was necessary for the application to living organisms both plant and animals, physiological chemistry relating to the cell membrane characteristics, along with pharmacological chemistry and analytical chemistry, with knowledge of the chemistry of chelation characteristics permitted the inventor to determine this unique application to the family of compounds described more fully hereinafter. This was a result of over eight years of research and experimentation.

Only after the inventor's discovery and application of these N-substituted amino acids and their therapeutic properties did the inventor become aware of N,N-dimethyl derivatives in an article by R. E. Bowman and H. H. Stroud. This article related to the preparation of certain of these derivatives in an optically active form to permit laboratory study and analysis of the basic structure of such compounds. Only dimethyl acid derivatives, N,N-dimethyl L-aspartic acid, N,N-dimethyl-DL-aspartic acid, N,N-dimethyl-L-glutamic acid were set forth specifically in R. E. Bowman and H. H. Stroud, Journal of Chemical Society (a British publication), 1950, a three-part article bearing the numbers 272, 273, and 274 and found at pages 1342 through 1351, and bearing the general title "N-substituted Amino-acids" and the three parts bearing the respective part titles of "A New Method of Preparation of Dimethyl Amino-acids" and "The Reductive Alkylation of Amino-acids" and "The Reductive Alkylation of Some Di- and Tri-peptides. A New Method of Determining the 'End Amino-acid' in Polypeptides". Pages 1343 and 1345 of the above article are especially pertinent in this connection and page 1345 also cites an earlier reference which is indicated to show previous obtaining of N,N-dimethyl-DL-aspartic acid by earlier researchers as reported in the earlier reference there cited, presumably by an at least somewhat different method.

However, to the best of my knowledge, this article by Bowman and Stroud does not suggest any use for such compounds, let alone the specific preparation I use for my topical application to the skin. Moreover, the literature clearly shows that the only consideration of amino acids or their derivatives relates to the biological or nutritional activity as it regards protein.

Thus, there is no teaching or suggestion that such compounds have any practical application. Moreover, the earlier teachings with regard to the salicylate compounds and the increased molecular weight teaches away from such an approach. Therefore, the analgesic and anti-inflammation characteristics of these modified amino acids is totally unexpected and consitutes the basis for this invention.

Furthermore, it has been observed that aside from the pharmacological potential for this family of compounds, other applications are feasible. For example, the solubility, miscibility and sequestration-chelation characteristics suggest uses as detergents, wetting agents, emulsifiers, defoamers, and dispersants for a wide range of industrial and agricultural applications. The wide range of applications for EDTA (ethylene-diamine-tetraacetic-acid) may be duplicated by these compounds. Oil-spill cleanup, enhancement of micro-nutrient take-up solutions for plants, and pesticide adjuvants, may represent potential. The bio-degradable capability for such compounds gives them great significance in the industrial-agricultural eco-system relationships now receiving extensive study.

SUMMARY OF THE INVENTION

The present invention relates to certain medical applications involving specific derivatives of amino acids.

The preferred treatment process involves alleviating certain undesirable localized symptoms of rheumatoid arthritis by applying this medication topically to the skin surrounding the affected areas of the human body, or similarly for veterinary applications.

These undesirable localized symptoms of tissue trauma involve pain, swelling, or edema, and inflammation per se, including concomitant local heat and redness, as well as a tendency toward spasm and reduced mobility resulting from these symptoms.

The most preferred application for this purpose includes an effective amount of N,N-dimethyl aspartic acid or N,N-dimethyl glutamic acid or any pharmaceutically acceptable salt of either of the foregoing, such as especially a magnesium, sodium, potassium, ammonium or calcium salt, or a mixture or mixtures of any of the foregoing, the preparation having a pH making it physiologically acceptable to the skin, such as especially a pH of about 5 through 7 and most preferably a pH of about 6. The medication may also include a physiologically acceptable maskant, such as benzyl alcohol, methyl valerate, methyl isovalerate, ethyl isovalerate, isopentyl acetate, isopentyl valerate, or ethyl butyrate to mask any objectionable amine aroma.

In general topical use is preferable, but an injectable form involving a dilution to 10% with for example sterile water, into the localized part of the body involved may be employed. To a limited extent this may be an advantage, where an unusually complicated part of the body such as happens to be the knee or hip is involved and the quickest practical relief happens to be desired. This particular proportion is of course exemplary and preferred, rather than the only proportion capable of injectable use. The dilution preferably with distilled water, as well as the water being sterile, as stated above, to 10% (by volume STP) starts with the preparation in the form which it assumes at the end of the preferred process of manufacture given specifically as an example hereinafter, being treated as the 100% on which the 10% is calculated.

Not preferred, but also possible, is oral administration of effective amounts of any of the above compounds or a mixture or mixtures thereof in a form physiologically acceptable to the gastro-intestinal tract.

The form of such oral administration would preferably be in enteric coated tablets or enteric encased capsules. While dosage amounts for oral administration can be flexible, depending on the judgment of the physician and the size and need of the patient, a child of course getting a proportionately less amount, the suggested preferred amount for normal size adults in such solid oral form would be most preferably 50 milligrams per day, divided up into four capsules or four tablets at spaced times and the preferred range would be 25 through 50 milligrams per day-similarly divided. If despite the above preferences, nevertheless for any reason the physician should decide to use the preparation orally in liquid form, he should start with the same dilution to 10% (by volume STP), pH 6, the 10% being calculated in the same way as the injectable, as will be found above, and for normal size adults use one tablespoon daily, in three evenly divided spaced doses, and adjust in the light of results.

While the primary and most important thing involved is rheumatoid arthritis as above, the preparations of the present invention are also useful in the same way and by the same methods against other arthritides and also in general against other inflammatory syndromes, as well as aches of a general localized nature in traumatized tissue and from musculo-skeletal disorders, and also neuro-muscular spasm.

Furthermore, in addition to the most preferred compounds above, also preferred but not as much so is similar use of similar compounds in which to get the desirable amount of dimethyl and/or methyl derivatives, I either wholly use or add to the most preferred dimethyl derivatives previously mentioned N,N-dimethyl hydroxyglutamic acid, a non-naturally occurring compound, or N-monomethyl aspartic, glutamic or hydroxyglutamic acid, or a physiologically acceptable salt or salts of any of these also preferred acids, or a mixture or mixtures of any of these also preferred dimethyl and/or methyl derivatives.

Also suitable and useful but not preferred is similar use of similar compounds in which to get the desirable amount of dimethyl and/or methyl derivatives I either wholly use, or add to the dimethyl and/or methyl derivatives already mentioned N,N-dimethyl alpha amino adipic acid or N,N-dimethyl serine, or N,N-dimethyl threonine, or a corresponding N-monomethyl compound, or one or more of the physiologically acceptable salts of these various named derivatives not preferred or a mixture or mixtures of any of these dimethyl and/or methyl derivatives not preferred.

Since the theoretical basis for the therapeutic actions of these compounds is in part a function of molecular size, it is apparent that other alkyl groups could likewise be substituted in mono and/or dialkyl forms to effect the same activities of the substituted amino acid derivatives. For example, alkyl groups such as ethyl, propyl, butyl and amyl alone or in combination could be used.

The invention accordingly comprises the features of construction, combination of elements, and arrangement of parts that will be exemplified in the construction hereinafter set forth, and the scope of the invention will be indicated in the claims.

DETAILED DESCRIPTION OF THE PREFERRED EMBODIMENT

Going into various specifics in connection with what is already stated in the foregoing Summary of Invention, the particular dimethyl and/or methyl acid derivatives included in the above preparations may be in any one of the three forms L, DL, or D, as to which the L form is somewhat preferred.

On my part, the preferred method for the synthesis of these and other dimethyl compounds above involved comprises refluxing an aqueous solution of one (or more) of the fundamental amino acid(s) crystals, such as for example the original aspartic or glutamic acid in question, with somewhat more than 2 mols by proportion each of formalin (formaldehyde) and formic acid. Reaction is at about 100°-110° C., under slightly reduced pressure. Conversion commences within ½ hour, with formation of a yellow to brown-colored liquid product. The resultant liquid is both oil and water miscible. This refluxing is completed in 1 to 2 hours, with excess formaldehyde and formic acid being drawn off by aspiration. The resultant mixture is partly neutralized to preferably pH 6.0 by the addition of sodium carbonate. Where as already indicated, some other pharmaceutically acceptable salt might be desired, needless to say, some other suitable compound yielding the other salt should be used, such as the corresponding potassium (or even magnesium) compound or a suitable calcium compound, such as limewater (i.e., a suitable alkaline water solution of Ca(OH)$_2$, but ammonium salts, while usable if necessary, are definitely not preferred.

The following is a typical formula for producing one of the derivative compounds, in this case the N,N-dimethyl derivative of aspartic acid:

EXAMPLE

| | |
|---|---|
| Aspartic Acid (mol wt. 133) CP | 133 grams |
| Formic Acid 1.22 CP | 80 ml |
| Formalin 37% 1.08 CP | 150 ml |
| Water (distilled) to make | 1 liter, |
| | and then |
| Sodium Carbonate (mono-hydrate) CP | 124 grams |

In making up the foregoing preparation, benzyl alcohol, methyl valerate, methyl isovalerate, ethyl isovalerate, isopentyl acetate, isopentyl valerate or ethyl butyrate for use as already indicated is added after the water in a quantity of 1/20% to and including 1% by weight of what is already present (including the water present), or most preferably ¼ of 1% by weight of the same.

An alternative but more complex and expensive procedure for the synthesis involves the reaction of the amino acid(s) with formaldehyde and hydrogen, using palladium-charcoal (carbon) catalyst.

Where some other dimethyl derivative is desired, needless to say, the starting material will be the original amino acid corresponding to it and adjustment will be made for the difference in respective molecular weights involved, with further adjustment to include only half as much of the neutralizing material in cases where there is only one carboxyl group in the original acid, in contrast to aspartic and glutamic acid, which of course each has two carboxyl groups.

If part or all monomethyl compounds are desired in a particular case, this can be secured by reducing the amount of formic acid and formalin used in the process.

Thus, it is envisioned that the medication and method of treatment may comprise one or more of the following:
N,N-dimethyl aspartic acid;
N,N-dimethyl glutamic acid;
N,N-dimethyl hydroxyglutamic acid;
N,N-dimethyl alpha amino adipic acid;
N,N-dimethyl serine;
N,N-dimethyl threonine;
N-monomethyl aspartic acid;
N-monomethyl glutamic acid;
N-monomethyl hydroxyglutamic acid;
N-monomethyl alpha amino adipic acid;
N-monomethyl serine;
N-monomethyl threonine;
Physiologically acceptable salt or salts of the above.

Where the application is topical on the skin, I prefer simply applying directly in the form which it reaches as a result of my above preferred method of manufacture, with any substantial remaining formic acid and formalin having been removed, as by aspiration as already indicated. Small amounts of formalin and/or formic acid appear not to interfere with the application formulations.

However, so long as a proper pH is maintained, it will be understood that a more concentrated or dilute medication may be utilized.

These medications when used topically on the skin, in addition to being used directly as above, can be used diluted or undiluted as lotions, ointments, or creams with suitable additions to produce such forms. For example, one preferred such form of use is as an ointment using Carbowax, a well known proprietary brand of nonvolatile polyethylene glycol which is normally solid in the higher molecular weight ranges, as to which the exemplary and preferred formulation can well be by weight:

30% of the medication specifically as made up in the example, including the preferred proportion of benzyl alcohol maskant (or other acceptable maskants)
1% of glycerine
4% of Carbowax 600 (polyethylene glycol having a molecular weight of 570 to 630 which is normally liquid at room temperature)
65% of Carbowax 6000 (polyethylene glycol having a molecular weight of 7000 to 9000 and a melting range of 58°-62° C.)

In this example, the components can be mixed at around 65° C., at which temperature the polyethylene glycol 6000 will no longer be solid.

Where a liquid such as the medication undiluted or diluted directly applied or in the form of a lotion is used for topical application to the skin, this should be applied to the clean area desired and allowed to dry, and washing of that area should be avoided for an hour or two. More specifically, the preferred method of application in such a case should involve complete wetting of the area without dripping two or three times a day until complete relief of the symptoms of pain and swelling is secured. It is not necessary in connection with the topical application to massage the area involved in connection with the topical application.

Where topical application by ointment is desired, the same frequency should be used.

While of course the total amount applied topically to the skin in any one application will vary greatly depending on such things as especially the total area to which the limited or widespread location of the localized symptoms call for it to be applied, it will be found that in most cases not more than about one half a cubic centimeter of the most preferred liquid medication will be required for any one application.

Where application is by injection, it should be done once a day until suitable relief is secured.

As will be recognized, the amount inserted by any one injection will be limited in any particular case to the amount which it is practical to insert in one injection in that particular place without hurting the patient substantially more than is inherent in the very fact of injection, according to well known principles. Thus it is essentially a matter to be determined according to the good judgment of the physician or registered nurse who is doing the injecting. However, subject to the above overriding consideration, a preferred range to inject in any one injection when it is within the above guidelines is one-tenth cubic centimeter through one-half cubic centimeter, with the smallest above amount being used when the preparation is in concentrated form.

While the validity of this invention does not depend on the correctness of any theory which may tend to explain or underlie it, and I am not necessarily certain of the correctness of any such theory, I believe that any beneficial results secured in at least the alleviation of the undesirable localized symptoms of rheumatoid arthritis may very well be related to any oil and water miscibility and solubility of any compounds involved which could involve miscibility in lipids for example and thus would be likely to assist cell wall penetration, and also in any ability as a matter of sequestration to interact with the metal ions present to form chelate complexes, after penetration into the inflamed tissue, as well as their small molecular volumes, secured by the low molecular weights, which may well be an important factor in any oil and water miscibility and solubility as well as any ability to penetrate the cell wall, these matters of any oil miscibility and solubility and sequestration and chelation capability being things which so far as I known I have been the one to discover and which have formed an important part of my thinking in connection with the invention.

Other N-monoalkyl or N,N dialkyl derivatives such as ethyl, propyl, butyl, or amyl may be substituted for methyl. Corresponding homologues of formaldehyde such as acetaldehyde, propionaldehyde, butyraldehyde or amylaldehyde may be substituted to obtain the alkyl compound desired.

As previously set forth, applicant has ascertained that this family of compounds exhibits greatly enhanced carrier properties and/or potentiation of biochemical activity in a biological entity for use in a wide range of applications such as in estrogen, vitamin and mineral therapy, salicylate therapy, enhancement of micronutrient take-up solutions for animals, plants or as pesticide adjuvants.

It will thus be seen that the objects set forth above, and those made apparent from the preceding description are efficiently attained and since certain changes may be made in the above construction without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which as a matter of language, might be said to fall therebetween.

Now that the invention has described, what is claimed is:

1. A method of reducing tissue trauma, neuro-muscular spasms, and musculo-skeletal disorders in an animal, by administering to said animal an effective amount of a compound which comprises one or more N-monoalkyl and/or N-N, dialkyl derivatives of the following amino acids:
   aspartic acid;
   glutamic acid;
   hydroxyglutamic acid;
   alpha amino adipic acid;
   serine;
   threonine;
physiologically acceptable salt or salts of the above.

2. The method of claim 1 wherein said N-monoalkyl and/or N-N dialkyl derivatives comprises methyl.

3. The method of claim 1, wherein said N-monoalkyl and/or N-N dialkyl derivatives comprise ethyl.

4. The method of claim 1, wherein said N-monoalkyl and/or N-N dialkyl derivatives comprise propyl.

5. The method of claim 1, wherein said N-monoalkyl and/or N-N dialkyl derivatives comprise butyl.

6. The method of claim 1, wherein said N-monoalkyl and/or N-N dialkyl derivatives comprise amyl.

7. A method of claim 1 in which said medication of claim 1 has a pH in the range from about 5 to and including about 7.

8. A method of claim 1 in which said medication has an effective proportion of maskant for any objectionable amine aroma which may otherwise be noticeable in said medication.

9. A process for producing a medication and product for the reduction of tissue trauma, neuro-muscular spasms, musculoskeletal disorders in an animal, and/or a potentiator of bio-chemical activity in a biological entity having the characteristics of oil and water miscibility and solubility, and chelation-sequestration to enhance penetration and absorption comprising:
   (1) refluxing an aqueous solution of one or more amino acids with formaldehyde (formalin) and formic acid;
   (2) aspiration of excess formaldehyde and formic acid.

10. The process of claim 9 wherein said refluxing is at 100° C. to 110° C.

11. The process as in claim 10 wherein said refluxing is under a slightly reduced pressure.

12. The process as in claim 9 wherein said resultant mixture is neutralized to preferably pH 6.0.

* * * * *